(12) United States Patent
Geisel

(10) Patent No.: US 8,542,025 B2
(45) Date of Patent: Sep. 24, 2013

(54) EMBEDDABLE MOISTURE SENSOR, MEASUREMENT DEVICE AND METHOD OF USE THEREOF

(76) Inventor: Donald J. Geisel, Clifton Park, NY (US)

( * ) Notice: Subject to any disclaimer, the term of this patent is extended or adjusted under 35 U.S.C. 154(b) by 714 days.

(21) Appl. No.: 12/578,897

(22) Filed: Oct. 14, 2009

(65) Prior Publication Data

US 2010/0090713 A1 Apr. 15, 2010

Related U.S. Application Data

(60) Provisional application No. 61/196,021, filed on Oct. 14, 2008, provisional application No. 61/198,664, filed on Nov. 8, 2008.

(51) Int. Cl.
*G01R 27/26* (2006.01)

(52) U.S. Cl.
USPC .......................... 324/668; 324/664; 324/667

(58) Field of Classification Search
USPC ....................................................... 324/668
See application file for complete search history.

(56) References Cited

U.S. PATENT DOCUMENTS

| | | | |
|---|---|---|---|
| 3,906,340 A | | 9/1975 | Wingfield et al. |
| 4,297,874 A | * | 11/1981 | Sasaki ............................. 73/73 |
| 4,552,570 A | * | 11/1985 | Gravatt ........................... 95/10 |
| 5,621,669 A | * | 4/1997 | Bjornsson ....................... 702/85 |
| 5,666,061 A | | 9/1997 | Assenheim |
| 6,677,859 B1 | | 1/2004 | Bensen |
| 6,963,205 B2 | * | 11/2005 | Lundstrom et al. ............ 324/664 |
| 7,068,050 B2 | * | 6/2006 | Steele et al. ................... 324/640 |
| 7,296,461 B2 | | 11/2007 | Barguirdjian et al. |

OTHER PUBLICATIONS

Han, Sangwook et al., "Wireless power transfer using resonant inductive coupling for 3D integrated circuits", University of Michigan, 2010, http://www.eecs.umich.edu/wics/publications/Han_3DIC2010.pdf, p. 1-5.*
Kuphaldt, "Q and Bandwidth of a Resonant Circuit", All About Circuits, vol. II—AC Circuits, p. 1-5.*
Storr, Wayne, Basic Electronics Tutorials, Electronics-Tutorials.ws, "Maximum Power Transfer Theorem", p. 1-4.*

* cited by examiner

*Primary Examiner* — Thomas Valone
(74) *Attorney, Agent, or Firm* — Schmeiser, Olsen & Watts, LLP

(57) ABSTRACT

Disclosed herein is a method of interrogating a resonant circuit that includes embedding a resonant circuit into a material, wherein a dielectric of a capacitor of the resonant circuit is the material. The method includes remotely determining the resonant frequency of the electrical circuit with a measurement device, wherein the determining is accomplished automatically. Finally, the method includes remotely automatically determining at least one of an estimated or precise resistance of the resonant circuit, an estimated or precise quality factor of the resonant circuit, and an estimated or precise voltage ratio of the resonant circuit, wherein the voltage ratio is a ratio of a voltage of the energy absorbed by the receiver at resonance and a voltage of the energy absorbed by the receiver at a fixed frequency shift from resonance.

17 Claims, 4 Drawing Sheets

EMBEDDABLE MOISTURE SENSOR, MEASUREMENT DEVICE AND METHOD OF USE THEREOF

RELATED MATTER

This application is a non-provisional claiming priority to two commonly owned U.S. Provisional Patent Applications: Ser. No. 61/196,021, filed Oct. 14, 2008, of Donald J. Geisel, entitled "EMBEDDED MOISTURE SENSOR," and Ser. No. 61/198,664, filed Nov. 8, 2008 of Donald J. Geisel, entitled "SUB-SURFACE MOISTURE METER," the disclosures of which are herein incorporated by reference to the extent not inconsistent with the present disclosure.

FIELD OF THE INVENTION

The subject matter disclosed herein relates generally to moisture detection. More particularly, the subject matter relates to an embeddable moisture sensor, a measuring device, and a method of use thereof.

BACKGROUND OF THE INVENTION

Moisture detection in insulating or other non-metallic or partially metallic materials is of concern due to potential failure or degradation of an insulator from water contamination. Failure of the insulator due to moisture contamination may occur because of a simple deterioration of the insulator, an electrical malfunction, or a loss of thermal efficiency. Examples of common insulators include construction walls, roofs, heat shields and high voltage insulators. Additionally, moisture detection may be of importance in construction materials such as concrete. This is because moisture detection may help predict hydration or curing of these construction materials. Current methods of detecting moisture are generally non-destructive and typically involve a probing field. These methods attempt to fully analyze the insulator through a test surface examination. Some current testing apparatus' use a capacitance probe or a radio field, while other current testing apparatus' use a nuclear source. All of the above testing apparatus' must physically make contact with the surface. Another current testing apparatus uses needle probes which penetrate the surface. All of the non-destructive devices must first probe a surface zone before penetrating an inner zone. As a result of this limitation, the true zone of interest, which may be several inches beneath a surface, may be masked.

Thus, an improved method and apparatus to examine an embeddable environment where moisture is suspected would be well received in the art.

BRIEF DESCRIPTION OF THE INVENTION

According to one embodiment of the present invention, a moisture sensor comprises an electrical circuit embeddable into a material and having an inductor, a first capacitor and a second capacitor, and wherein the dielectric of the second capacitor is configured to be the material when the electrical circuit is embedded, and wherein the capacitance of the first capacitor is larger than the capacitance of the second capacitor such that the resonant frequency of the electrical circuit is not substantially altered by changes in capacitance of the second capacitor.

According to another embodiment of the present invention, a measurement device comprises a transmitter configured to transmit energy by sweeping across a frequency range; a receiver configured to remotely measure energy absorbed by a resonant circuit that is in a field of the transmitted energy; a means for automatically determining a resonant frequency of the resonant circuit from the energy absorbed by the receiver; and a means for automatically determining at least one of: an estimated or precise resistance of the resonant circuit; an estimated or precise quality factor of the resonant circuit; and an estimated or precise voltage ratio of the resonant circuit, wherein the voltage ratio is a ratio of a voltage of the energy absorbed by the receiver at resonance and a voltage of the energy absorbed by the receiver at a fixed frequency shift from resonance.

According to yet another embodiment of the present invention, a method of interrogating a resonant circuit comprises embedding a resonant circuit into a material, wherein a dielectric of a capacitor of the resonant circuit is the material; remotely determining the resonant frequency of the electrical circuit with a measurement device, wherein the determining is accomplished automatically; and remotely automatically determining at least one of: an estimated or precise resistance of the resonant circuit; an estimated or precise quality factor of the resonant circuit; and an estimated or precise voltage ratio of the resonant circuit, wherein the voltage ratio is a ratio of a voltage of the energy absorbed by the receiver at resonance and a voltage of the energy absorbed by the receiver at a fixed frequency shift from resonance.

BRIEF DESCRIPTION OF THE DRAWINGS

The subject matter which is regarded as the invention is particularly pointed out and distinctly claimed in the claims at the conclusion of the specification. The foregoing and other features and advantages of the invention are apparent from the following detailed description taken in conjunction with the accompanying drawings in which:

DETAILED DESCRIPTION OF THE INVENTION

A detailed description of the hereinafter described embodiments of the disclosed apparatus and method are presented herein by way of exemplification and not limitation with reference to the Figures.

Figure 1:
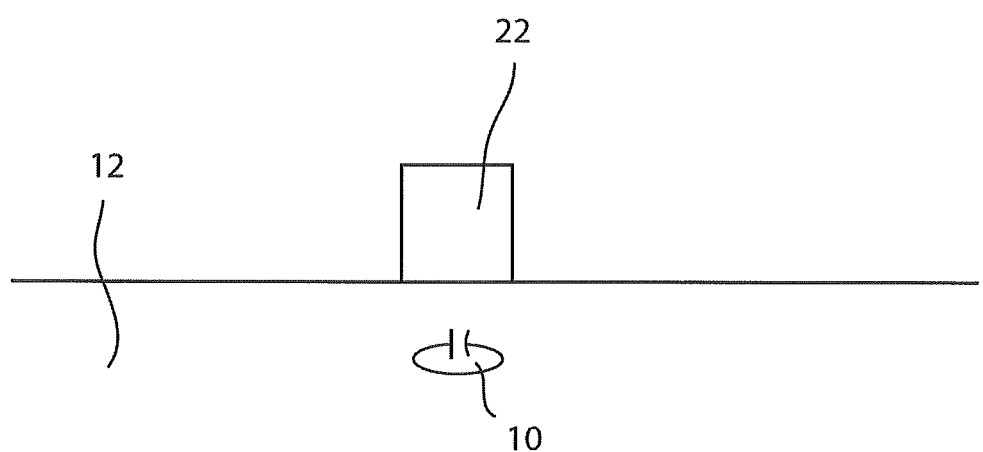
FIG. 1 depicts a moisture sensor embedded in a material body with a measuring device above the material in accordance with one embodiment of the present invention.

Referring to FIG. 1, a moisture sensor 10 is shown embedded in a material 12 according to one embodiment of the invention. The moisture sensor 10 includes a having an inductor 16, a first capacitor 18 and a second capacitor 20 with internal loss Rp (shown in FIGS. 2 and 3). A measurement device 22 is located above the surface of the material 12. The moisture sensor includes a transmitter 24 and a receiver 26 (shown in FIG. 4). The transmitter 24 of the measurement device 22 is configured to transmit energy by sweeping across a frequency range. The resonant circuit 14 of the moisture sensor 10, and more particularly the inherent loss due to the resistance in the electrical circuit 14, absorbs this transmitted energy from the measurement device 22 at and near the resonant frequency of the moisture sensor 10. The receiver 26 of the measurement device 22 is configured to remotely measure this energy absorbed by the resonant circuit 14. The measurement device 22 is then configured to automatically and remotely determine a resonant frequency of the resonant circuit 14 from the energy absorbed by the receiver 26. Once the resonant frequency is determined, the measurement device 22 is configured to automatically and remotely determine an estimated or precise value that correlates to the moisture in the material 12. For example, this value may be a resistance of the resonant circuit 14, a quality factor of the resonant circuit 14. Alternately, this moisture-indicating value may be a voltage ratio of the resonant circuit 14, wherein the voltage ratio is a ratio of a voltage of the energy absorbed by the receiver 26 at resonance and a voltage of the energy absorbed by the receiver 26 at a fixed frequency shift from resonance. The measurement device 22 may be then configured to display one or more of these moisture-indicating values. Thus, a user may embed one or more of these moisture sensors 10 into the material 12 and later determine if the material 12 has been contaminated by moisture.

Figure 2:
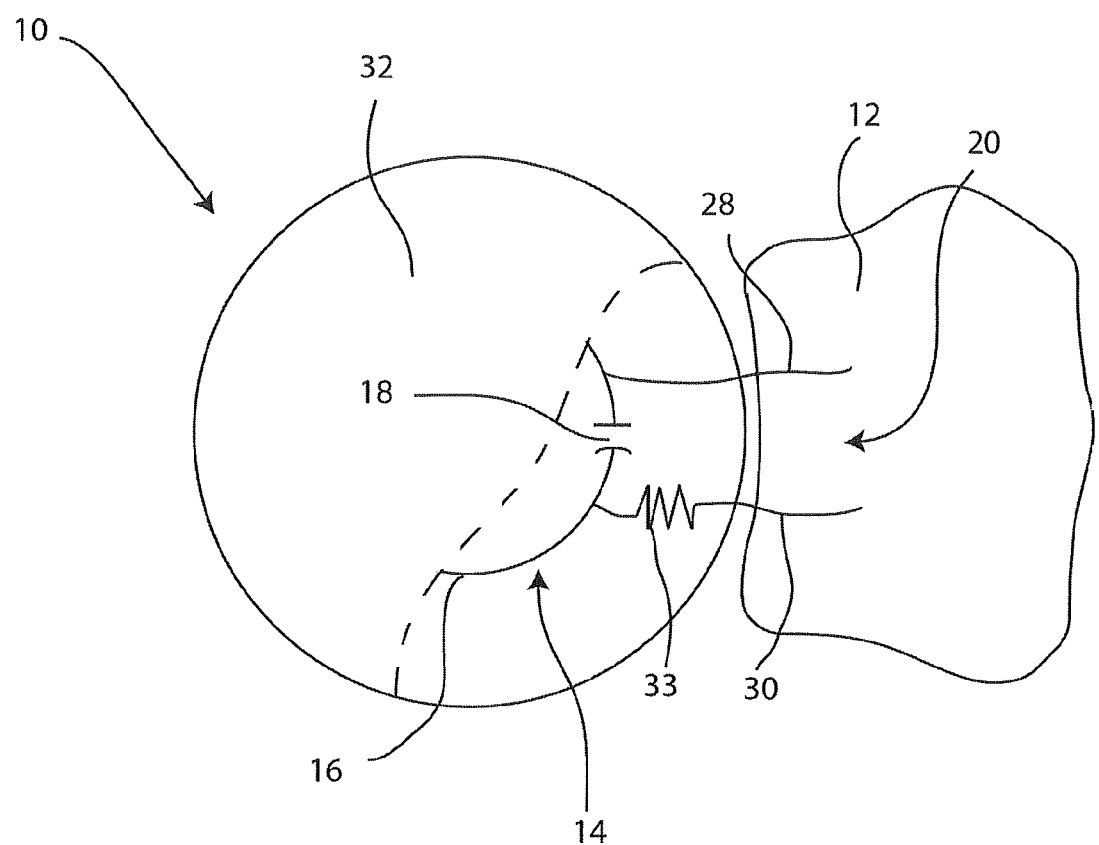
FIG. 2 depicts the moisture sensor of FIG. 1 in accordance with one embodiment of the present invention.
Figure 3:
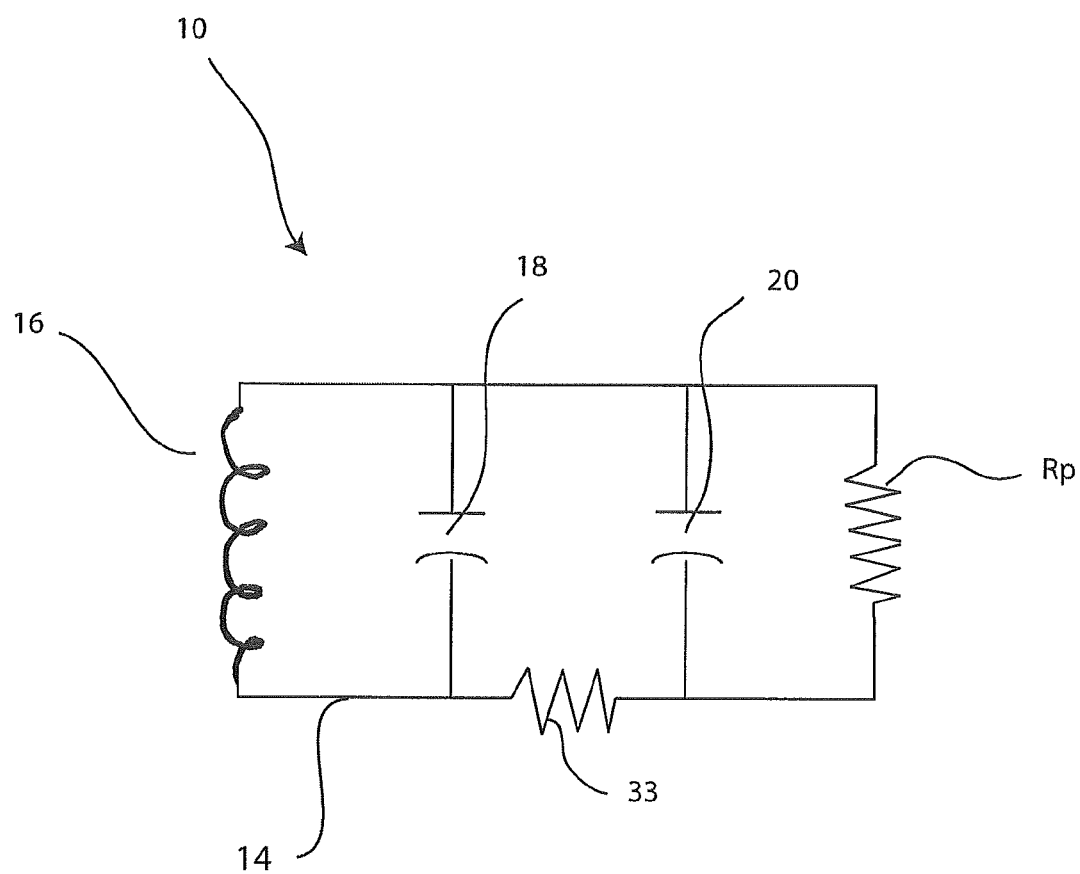
FIG. 3 depicts an electrical equivalent of the moisture sensor of FIGS. 1 and 2 in accordance with one embodiment of the present invention.

Referring now to FIG. 2, a cut-away view, shows the moisture sensor 10 is shown according to one embodiment of the present invention. The resonant electrical circuit 14 of the moisture sensor 10 is shown with the inductor 16, the first capacitor 18 and the second capacitor 20 connected in parallel. FIG. 3 depicts the symbolic electrical equivalent of this parallel circuit. The inductor 16 may be a wire having a plurality of loops, as is commonly known in the art. The first capacitor 18 may be a typical capacitor having glass, mica, or ceramic dielectrics or the like. The second capacitor 20 is shown including two leads 28, 30 extending from the electrical circuit 14 such that the material 12 becomes a dielectric of the second capacitor 20 when the moisture sensor 10 is embedded. The second capacitor 20 may also be any other appropriate contact elements. For example, the second capacitor 20 may simply comprise two portions of the wire of the inductor 16 that are stripped of insulation, thereby providing contact with the material 12.

Whatever the configuration of the first and second capacitors 18, 20, the capacitance of the first capacitor 18 is larger than the capacitance of the second capacitor 20 such that the resonant frequency of the electrical circuit 14 is not substantially altered by changes in the capacitance of the second capacitor 20. The resonant frequency of the electrical circuit 14 thereby changes very little due to the relative moisture of the material 12. This feature may allow the measurement device 22 to more easily scan for the resonant frequency of the electrical resonant circuit 14. For example, the first capacitor 18 may have a capacitance larger than the second capacitor such that the resonant frequency of the resonant circuit 14 only fluctuates between 17 MHz to 18 MHz depending on the moisture level of the dielectric material 12. Thus, the transmitter 24 may only be required to scan across a very narrow and predetermined frequency range.

It should be understood that the moisture sensor 10 may be embeddable in any material, such as concrete, asphalt, a thermal insulator, and air. For example, the moisture sensor 10 may be embeddable in an asphalt bridge construction as the asphalt is being poured. In order to protect the integrity of the inductor 16 and the first capacitor 18 in these environments, the moisture sensor 10 may be surrounded by an electrically insulated protective case 32. The protective case may be made from plastic, a composite or any other appropriate insulating material. The leads 28, 30 of the second capacitor 20 may extend outside of this electrically insulated protective case 32.

The moisture sensor 10 may also include a limiting resistor 33. The limiting resistor 33 may allow the resonant circuit 14 to work even when the surrounding material 12 is contaminated by water mixed with salts. Without the limiting resistor 33, the resonant circuit 14 is liable to be shorted such that the measurement device 22 may not be able to locate it. While the exemplary embodiment referred to herein is a parallel circuit, it should be understood that a series connection of these elements 16, 18, and 33 is also contemplated.

FIG. 3 is an equivalent electrical circuit of the moisture sensor 10. The components of the equivalent circuit include the inductor 16 and the first capacitor 18 to form resonant circuit 14. External contacts are formed by the second capacitor 20 with its internal loss resistance Rp. It should be understood that the second capacitor 20 and the internal loss resistance Rp are a single equivalent element. A limiting resistor 33 prevents the quenching of resonant circuit 14 if the losses of the external elements become substantial. This then allows the moisture sensor 10 to be still functional and able to be located by the measurement device 22. Those skilled in the art are aware of additional losses in the inductor 16 and the first capacitor 18. However, these losses will be small in comparison to those of the external second capacitor 20 with its inherent loss resistance Rp.

Figure 4:
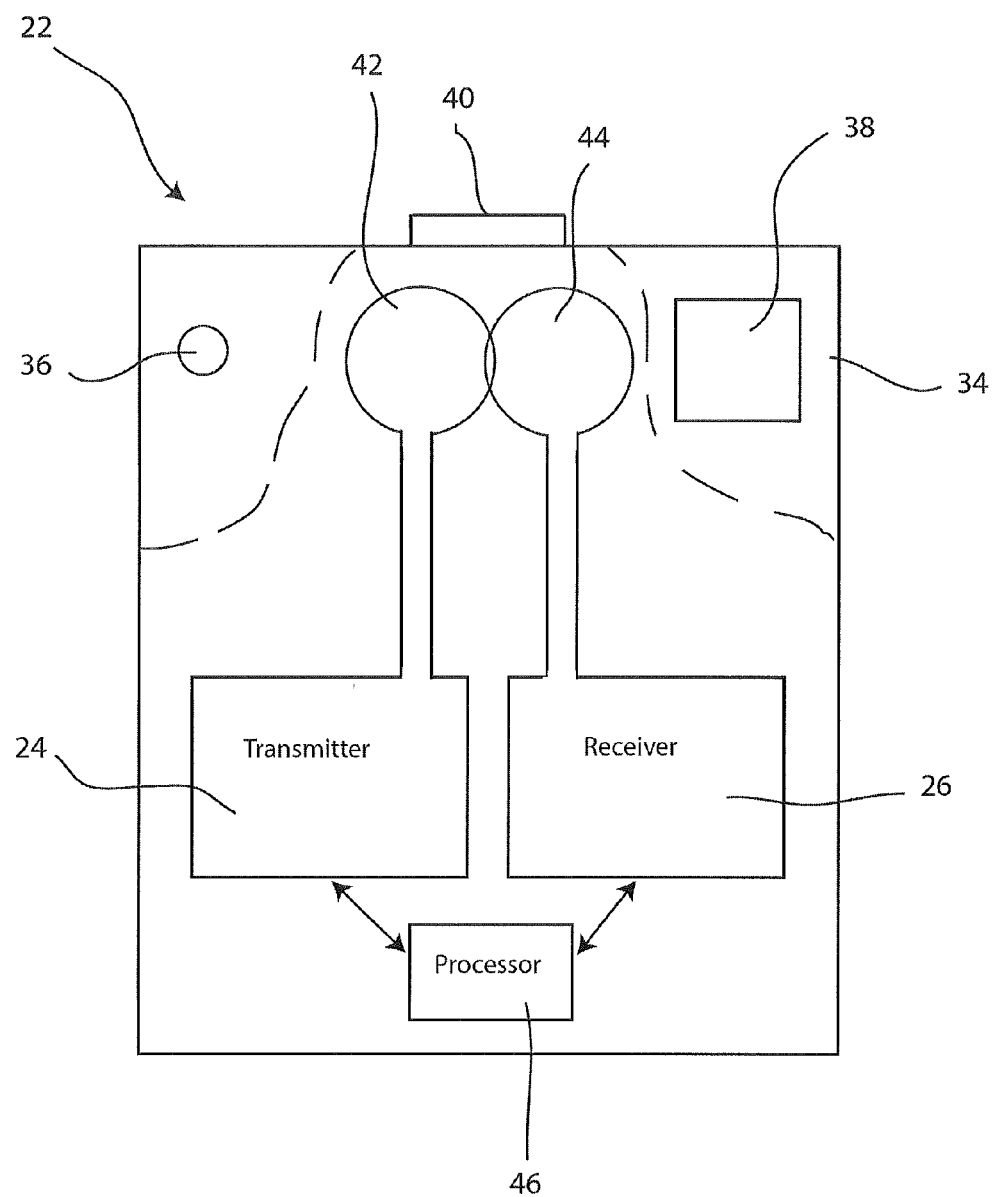
FIG. 4 depicts the measuring device of FIG. 1 in accordance with one embodiment of the present invention.

Referring now to FIG. 4, the measurement device 22 is shown according to one embodiment of the present invention. The components of the measurement device 22 may be housed within a housing 34. The housing 34 may include one or more buttons or other type of activation mechanisms 36 such that a user can control the function of the measurement device 22. The measurement device 22 may further include at least one screen 38 for displaying the resonant frequency and the values automatically and remotely calculated by the measurement device 22, such as the quality factor, the resistance of the resonant circuit, or a voltage ratio of the resonant circuit 14. The measurement device 22 still further may include a handle 40 in order to allow a user to more easily carry the measurement device 22 and situate it as needed in proximity to an embedded moisture sensor 10.

Housed within the housing 34 is the transmitter 24, the receiver 26. The transmitter 24 of the measurement device is shown having a first loop 42 while the receiver 26 includes a second loop 44. These loops 42, 44 are cross-coupled such that the signal received by the receiver 26 is nulled for a broad range of frequencies prior to being in the proximity of the resonant circuit 14 of the moisture detector 10. Thus, when the transmitter 24 transmits energy through the first loop 42, no signal is received by the receiver 26. However, when the two loops 42, 44 are put in the proximity of the resonant circuit 14, for example by being positioned directly above the resonant circuit loop, the receiver 26 then receives a signal. A third loop (not shown) is known to improve the nulling process and may allow for improved mechanical or electronic nulling to a level of null lower than two loops. The third loop may be positioned proximate to and its signals combined with that of either the first or second loop 42, 44 by electronic means to achieve improved nulling.

As previously described, the measurement device 22 is configured to automatically and remotely determine the resonant frequency of a resonant circuit, such as the resonant circuit 14 of the moisture sensor 10. The means by which the measurement device 22 performs this function may comprise a processor 46 that is in communication with the transmitter 24 and the receiver 26. The processor 46 may be one or more microprocessors, chips, computers, circuit boards or other the like. In order to determine the resonant frequency, the processor 46 may control the scanning of the transmitter 24 such that the transmitter 24 scans back and forth across a frequency range in response to the energy absorbed by the receiver 26 to determine the maximum energy absorbed by the receiver 26.

This maximum energy absorbed by the receiver 26 will correspond with the resonant frequency of a resonant circuit in the proximity, such as the resonant circuit 14 of the moisture sensor 10.

For example, if the resonant frequency of the resonant electrical circuit 14 is guessed to be around 18 MHz, the processor 46 may be configured to have the transmitter 24 automatically begin scanning from 17 MHz. During this scanning, the processor 46 may be configured to receive data from the receiver 26 corresponding to the energy received. As the frequency transmitted increases from 17 MHz, the receiver 26 will continue to receive higher levels of energy until the transmitter 24 is scanning at the resonant frequency of the resonant circuit 14. When the energy absorbed by the receiver 26 begins to decrease, the processor 46 may be configured to communicate to the transmitter 24 to begin reducing frequency. This back and forth scanning process may continue until the processor 46 determines the exact resonant frequency of the resonant circuit 14. This resonant frequency may then be displayed on the screen 38.

Once the resonant frequency is determined, the measurement device 22 may then automatically and remotely determine at least one moisture-indicating value relating to the moisture of the material 12 that comprises the dielectric of the second capacitor 20 of the resonant circuit 14. For example, the measurement device 22 may include a means for automatically and remotely determining an estimated or precise voltage ratio of the resonant circuit 14. This voltage ratio may be a ratio of the voltage of the energy absorbed by the receiver 26 at resonance and a voltage of the energy absorbed by the receiver 26 at a fixed frequency shift from resonance. In one case, this frequency shift may be a 3 db bandwidth frequency shift.

To determine this voltage ratio, 3 db bandwidth points (or half power points) may be utilized. The processor 46 may include a function that determines the exact 3 db bandwidth points from the data received from the receiver 26 during the resonant frequency finding scanning process. Alternately, estimated 3 db bandwidth points may be utilized. For example, in a case where the resonant frequency of the resonant circuit 14 is around 18 MHz, an automatic frequency shift of 0.4 MHz may be used to estimate where the 3 db bandwidth point is. This estimated frequency shift embodiment may reduce the complexity of the computations required to be performed by the processor 46 without reducing the accuracy of determining the relative moisture in the material 12.

The frequency shift may be initiated when a user presses the activating mechanism 36. When the frequency is shifted, the transmitter 24 automatically switches the transmitted frequency from the resonant frequency of the resonant circuit 14 to a shifted frequency. The processor 46 then receives data correlating to a voltage received by the receiver 26 after the frequency shift. The voltage ratio may then be determined by dividing the resonant frequency voltage with the voltage received after the frequency shift. This ratio may then be automatically displayed on the screen 38 of the measuring device 22. This voltage ratio is a good indicator of relative moisture in the material 12 because the voltage received by the receiver 26 after the frequency shift will be significantly more reduced when no moisture is present, and significantly less reduced when moisture is present. Thus, depending on the value of the voltage ratio displayed on the screen 38, the relative moisture in the material 14 may automatically and remotely be determined by a user.

While the voltage ratio is one moisture-indicating value, the measuring device 22 may also determine other values. For example, the measuring device 22 may determine an estimated or precise parallel resistance of the resonant circuit 14, or an estimated or precise quality factor of the resonant circuit 14. The measuring device 22 may find the 3 db bandwidth using the processor 46 as described hereinabove. Once the 3 db bandwidth is found, the quality factor may be determined by the processor 46 by dividing the resonant frequency by the 3 db bandwidth. This is an equation to find the quality factor that is known to those skilled in the art. Using standard abbreviations: $Q=Fc/BW$, where Q is the quality factor, Fc is the resonant frequency and BW is the 3 db bandwidth. The determined value for the quality factor may then be displayed on the screen 38. Quality factor may also be a good indicator of relative moisture, because quality factor will be reduced in the presence of moisture. The more relative moisture in the material 12, the lower the value will be for the quality factor of the resonant circuit 14.

Additionally, the resistance of the resonant circuit 14 may be determined by the measuring device 22 in a similar manner The parallel resistance of the resonant circuit 14 may then be found by dividing the quality factor by the capacitave reactance of the circuit. Again, this is another equation that is known to those skilled in the art. Using standard abbreviations: $Rp=Q/Xc$, where Rp is the parallel resistance, Q is the quality factor, and Xc is the capacitave reactance of the circuit. Capacitave reactance is a readily determinable value using the equation: $Xc=1/(2\pi(Fc)(C))$, where Fc is the resonant frequency and C is the capacitance. This resistance value may then be displayed on the screen 38 of the measurement device 22 to provide a user with insight into the moisture level in the material 12. Those skilled in the art are aware that loss in reactive elements can be represented by parallel, Rp or series Rs equivalent models. Likewise, those skilled in the art will recognize that resonance occurs in a series LC circuit and that such a circuit has a resistive loss and a quality factor. Such alternate representations and configurations are contemplated. Whatever the circuit configuration, the equivalent resistance of the circuit 14 may be an indicator of moisture when the interrogated circuit is a moisture sensor 10, as described herein. In this embodiment, as moisture levels change, the equivalent resistance of the circuit 14 will change.

Measuring the resistance Rp of an LC circuit, or the moisture sensor 10, "at resonance" allows for the resistivity of the material 12 to be calculated. Using standard abbreviations, the equation for resistivity is $\rho=Rp \times A/L$, where L is distance between external leads 28, 30 and A is the surface area of the leads 28, 30. Those skilled in the art understand that at resonance all L's and C's cancel out such that only resistance (either parallel or series) remains. Thus, pure capacitance of element 20 is ignored at resonance. One example is to employ the moisture sensor 10 to measure the resistivity of curing concrete to determine when a structure is able to bear load. It is known in the art that the resistivity of concrete varies by approximately a factor of 10 as it cures and that that such measurements are curing indicators. Due to variation of the resistivity with temperature of various materials in which the moisture sensor 10 may be placed, a temperature sensor may be employed to sense the temperature of the material 12. This may be used to calculate a temperature corrected resisivity value for improved instrument accuracy.

It should be understood that the measurement device 22 may be configured to display, on the screen 38, any appropriate value indicating relative moisture using the above described calculations. For example, the measurement device 22 may be configured to display a "relative moisture value" that is a function of one of the resistance, quality factor, or voltage ratio. For example, the processor 46 may be configured to manipulate the voltage ratio, resistance or quality factor determination such that a moisture percentage is actually displayed. For example, the processor 46 of the measurement device 22 may be pre-programmed to know that the possible values for quality factor may be between 500 in the presence of no moisture, and ½ at the highest moisture level possible. From this, a percentage of moisture may be determined using the following formula: M %=50/Q, where M % is the moisture percentage, and Q is the quality factor. The result of this calculation, a value between 0.1 and 100, may then be displayed on the screen 38. This may provide a user with a more understandable relative moisture indicator. It should be understood that other similar manipulations are possible and will be apparent to those skilled in the art.

It should be understood that the above described moisture sensor 10 and measurement device 22 may be used in combination to remotely and automatically determine a moisture-indicating value of a material 14. In one application, the moisture sensors 10 may be embedded permanently in asphalt or concrete beneath the asphalt during the pouring of the asphalt. A user may spray paint the surface of the asphalt to indicate that the moisture sensor is embedded directly below. Later, a user may return to the location of the moisture sensor and place the measurement device 22 directly above the spray painted mark. The measurement device 22 may touch the surface or a gap may be present. The measurement device 22, in other words, may be located above or near the surface. In one embodiment, the measurement device 22 may be held above the surface where the embedded sensor is located. Alternately, the user may use the measurement device 22 in a "search mode." In this embodiment, the measurement device 22 may sweep in frequency, as described hereinabove. When the measurement device 22 is in the proximity of the moisture sensor 10, it may then display a maximum value for resonant frequency. This displayed maximum value will increase as the measurement device 22 is brought more closely to the moisture sensor 10, until the user finds the location that is directly above the moisture sensor 10. The measurement device may then automatically and remotely determine a resonant frequency. A user may then press an actuation mechanism so that the measurement device automatically and remotely determines a moisture indicating value, as described hereinabove. This application may be similarly applied to building constructions. Control embeddable circuits (not shown) that do not include the leads 28, 30 extending outside the insulated protective case 32 may also be embedded in the material 14. These control embeddable circuits (not shown) may be used as a reference, as they will not be affected by changes in moisture.

Another unique market for the present invention may be to embed moisture sensors 10 within sealed boxes for shipping antiques. For example, the moisture sensor 10 may be embedded within a box in which an antique is being shipped. Before opening the box, the receiver of the box may then use the measurement device 22 to determine if the inside of the box is contaminated by water before accepting the antique from the shipper. These and other applications for the present invention will be understood by those skilled in the art.

Additionally, the measurement device 22 may be applied to other resonant circuits than a resonant circuit that is specifically configured for moisture detection, such as the moisture sensor 10. The measurement device 22 may be used to automatically and remotely determine and display the resonant frequency, quality factor, resistance, and voltage ratio of any resonant LC circuit, as described hereinabove. For example, it is known in the art that almost all communication and power conversion devices used by the industry or the military employs resonant circuits having inductors and capacitors. These devices have inherent losses and generate heat. The measurement device 22 may be configured to interrogate, remotely and automatically, these resonant LC devices.

Elements of the embodiments have been introduced with either the articles "a" or "an." The articles are intended to mean that there are one or more of the elements. The terms "including" and "having" and their derivatives are intended to be inclusive such that there may be additional elements other than the elements listed. The conjunction "or" when used with a list of at least two terms is intended to mean any term or combination of terms. The terms "first" and "second" are used to distinguish elements and are not used to denote a particular order.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

I claim:

1. A measurement device comprising:
   a transmitter configured to transmit energy by sweeping across a frequency range;
   a receiver configured to measure energy absorbed by a resonant circuit that is embedded in a material and that is in a field of the transmitted energy when the measurement device is above or near a surface of the material;
   wherein the measurement device is configured to automatically determine a resonant frequency of the resonant circuit from the energy measured by the receiver; and
   wherein the measurement device is configured to automatically determine at least one of:
      an estimated or precise resistance of the resonant circuit;
      an estimated or precise quality factor of the resonant circuit; and
      an estimated or precise voltage ratio of the resonant circuit, wherein the voltage ratio is a ratio of a voltage of the energy measured by the receiver at resonance and a voltage of the energy measured by the receiver at a fixed frequency shift from resonance.

2. The measurement device of claim 1, wherein the device is configured to remotely measure energy absorbed by a resonant circuit that is the embedded in a material.

3. The measurement device of claim 2, further comprising a comprising a screen for displaying an estimated or precise relative moisture of the material.

4. The measurement device of claim 1, further comprising a means for at least one of estimating and determining a 3 db bandwidth of the resonant circuit.

5. The measurement device of claim 1, wherein a fixed frequency shift is at or about a 3 db bandwidth point of the resonant circuit.

6. The measurement device of claim 1, further comprising an actuation mechanism configured to automatically shift the frequency of the transmitted energy to about a 3 db bandwidth point of the resonant circuit.

7. The measurement device of claim 1, further comprising a screen for displaying at least one of:
   the resonant frequency of the resonant circuit;

the estimated or precise resistance of the resonant circuit;
the estimated or precise quality factor of the resonant circuit; and
the estimated or precise voltage ratio of the resonant circuit.

8. The measurement device of claim 1, wherein the means for automatically determining the resonant frequency of the resonant circuit from the energy measured by the receiver comprises a processor in communication with the transmitter and the receiver.

9. The measurement device of claim 8, wherein the processor is configured to control scanning of the transmitter such that the transmitter scans back and forth across a frequency range in response to the energy measured by the receiver to determine the maximum energy absorbed by the resonant circuit, wherein the frequency at which the maximum energy is absorbed corresponds to the resonant frequency of the resonant circuit.

10. The measurement device of claim 1, wherein the transmitter and the receiver each include one or more loops, and wherein the loops are aligned such that the coupling between them is nulled for a broad range of frequencies when the loops are not in the proximity of a resonant circuit.

11. A method of interrogating a resonant circuit comprising:
embedding the resonant circuit in a material
automatically determining a resonant frequency of an electrical circuit with a measurement device that is above or near the surface of the material; and
automatically determining at least one of:
an estimated or precise resistance of the resonant circuit;
an estimated or precise quality factor of the resonant circuit; and
an estimated or precise voltage ratio of the resonant circuit, wherein the voltage ratio is a ratio of a voltage of the energy measured by the receiver at resonance and a voltage of the energy measured by the receiver at a fixed frequency shift from resonance.

12. The method of interrogating the resonant circuit of claim 11, further comprising displaying on a screen at least one of:
the resonant frequency of the electrical circuit;
the estimated or precise resistance of the resonant circuit;
an estimated or precise relative percentage of moisture in the material;
the estimated or precise quality factor of the resonant circuit; and
the estimated or precise voltage ratio of the resonant circuit.

13. The method of interrogating the resonant circuit of claim 11, further comprising sweeping, with a transmitter, across a frequency range.

14. The method of interrogating the resonant circuit of claim 11, further comprising locating a transmission loop of the measurement device directly above the resonant circuit.

15. The method of interrogating the resonant circuit of claim 11, further comprising determining a relative moisture level in the material.

16. The method of interrogating the resonant circuit of claim 11, further comprising embedding a resonant circuit into a material, wherein a dielectric of a capacitor of the resonant circuit is the material.

17. A system comprising:
a measurement device that includes a transmitter configured to transmit energy by sweeping across a frequency range and a receiver configured to measure energy absorbed by a resonant circuit that is embedded in a material and that is in a field of the transmitted energy when the measurement device is above or near a surface of the material, wherein the measurement device is configured to automatically determine a resonant frequency of the resonant circuit from the energy measured by the receiver, and wherein the measurement device is configured to automatically determine at least one of:
an estimated or precise resistance of the resonant circuit;
an estimated or precise quality factor of the resonant circuit; and
an estimated or precise voltage ratio of the resonant circuit, wherein the voltage ratio is a ratio of a voltage of the energy measured by the receiver at resonance and a voltage of the energy measured by the receiver at a fixed frequency shift from resonance; and
a moisture sensor that includes an electrical circuit embeddable into a material and having an inductor, a first capacitor and a second capacitor, and wherein the dielectric of the second capacitor is configured to be the material when the electrical circuit is embedded, and wherein the capacitance of the first capacitor is larger than the capacitance of the second capacitor such that the resonant frequency of the electrical circuit is not substantially altered by changes in capacitance of the second capacitor.

* * * * *